United States Patent [19]

Stanley

[11] Patent Number: 5,080,900
[45] Date of Patent: Jan. 14, 1992

[54] TREATMENT OF SKIN ULCERS WITH AN AQUEOUS EXTRACT OF OAK BARK ASH

[76] Inventor: R. Thomas Stanley, P.O. Box 1332, Auburndale, Fla. 33823

[21] Appl. No.: 509,824

[22] Filed: Apr. 17, 1990

[51] Int. Cl.$^5$ .............................................. A61K 35/78
[52] U.S. Cl. .............................. 424/195.100; 514/783
[58] Field of Search ...................... 424/195.1; 514/783

[56] References Cited

U.S. PATENT DOCUMENTS

| | | | |
|---|---|---|---|
| 37,901 | 3/1863 | Conway | 424/195.1 |
| 55,911 | 6/1866 | Salie | 424/195.1 |
| 202,246 | 4/1878 | Delisser | 424/195.1 |
| 256,847 | 4/1882 | Mayer | 424/195.1 |
| 4,059,695 | 11/1977 | Hirosari | 424/195 |
| 4,847,083 | 7/1989 | Clark | 424/687 |

OTHER PUBLICATIONS

Circa 1956, *Bencelok Ointment* label.
Circa 1989 *Bencelok Ointment* label.
King J. American Dispensatory, 8th ed., 1870, pp. 691–693.
Steinmetz, E. F., Codex Vegetabilis, 1957, #934, 936, 937, Amsterdam.
The Merck Index, 9th ed., 1976, #7389, Merck & Co., Rahway, N.J.

*Primary Examiner*—Ronald W. Griffin
*Assistant Examiner*—Ralph Gitomer
*Attorney, Agent, or Firm*—Rothwell, Figg, Ernst & Kurz

[57] ABSTRACT

In a method of treating skin ulcers, an ointment is applied to the ulcer which contains an aqueous extract of oak bark ash.

32 Claims, No Drawings

TREATMENT OF SKIN ULCERS WITH AN AQUEOUS EXTRACT OF OAK BARK ASH

BACKGROUND OF THE INVENTION

1. Field of the Invention

The present invention relates to the field of medically treating ulcers of the skin.

2. Description of the Background Art

Skin ulcers, such as abrasion ulcers, venostasis ulcers and decubitus ulcers, are open sores or lesions of the skin characterized by wasting away of tissue and sometimes accompanied by formation of pus.

Decubitus ulcers, sometimes called pressure wounds or bedsores, involve one of the most costly and dreaded skin conditions affecting particularly elderly geriatric patients. Such sores or ulcers are chronic, morbid conditions of the skin commonly found among the disabled, elderly and bedridden population of hospitals and nursing homes. It is estimated that one out of three people 65 years of age or older suffer or have suffered from this dreaded affliction. As predicted by the U.S. Census Bureau, by the year 2010 there will be over 65 million people in the United States in this geriatric age group. Not only does the affliction present a problem to the patient, but also to the institution caring for such individuals. The tremendous cost to the State and Federal Governments to cover the cost of caring for such wounds is staggering. It is estimated by recent reports summing up patient care hours for diagnostic related groupings, that the cost of pressure sore treatment amounts to as much as $62,500.00 per patient annually. This is indeed draining to the institutional health care budget.

Bedsores are often under treatment for months and sometimes even years with daily application of generally ineffective anecdotal therapies. Such anecdotal therapies range from mechanical devices such as cotton filled doughnuts, air filled mattresses, rotating beds, Clinitron beds, foam mattresses and air suspension mattresses, to a variety of topical preparations which are applied locally to the wound area including "debriders" or enzyme preparations to eat away the dead cells so that the living cells may survive, topical antibiotics to treat infections of the area, betadine washes, normal saline rinses, hydrogen peroxide soaks, wet to dry dressings, Debrisan ™, duoderm, occlusive dressings, silvadine ointments, elase ointments and travase ointment.

There remains an urgent need in the art for improved methods for treating ulcers of the skin.

SUMMARY OF THE INVENTION

In accordance with the present invention, a method for treating a skin ulcer comprises applying to the ulcer an ointment containing a therapeutically effective amount of an aqueous extract of oak bark ash.

DESCRIPTION OF THE PREFERRED EMBODIMENTS

It is surprisingly been discovered that an ointment containing a therapeutically effective amount of an aqueous extract of oak bark ash is effective in the treatment of skin ulcers such as abrasion ulcers, venostasis ulcers and decubitus ulcers.

The oak bark utilized to form the extract can be from Red Oak (*Quercus ruba L.*), Black Oak (*Quercus shumardi i Buckl.*), Scarlet Oak (*Quercus coccinea Muenchh.*), Pin Oak (*Quercus palustris Muencch.*), Willow Oak (*Quercus phellos L.*), and other species of the Erythrobalanus group.

The active ingredient of the ointment is derived from oak bark by burning the oak bark to convert it to ash, cooling the ash, screening the cooled ash to obtain an ash powder, mixing the ash powder with water to form a slurry, boiling the slurry and then filtering the residue to obtain a filtrate containing the desired extract. In preferred embodiments, one part screened ash is mixed with about four parts water to form the slurry, and the slurry is boiled for a period of from about 90 minutes to about 120 minutes. After filtering, the filtrate is concentrated by heating the filtrate to a temperature of about 150° F. to about 170° F., most preferably about 160° F., for from about four hours to about ten hours, depending on the desired concentration. In accordance with one embodiment, the filtrate is concentrated to about 20.5% ash extract to form an aqueous solution of oak bark extract.

Although an ointment containing this extract has been commercially available for some time, it has unexpectedly been found to be efficacious in the treatment of skin ulcers.

In preferred embodiments, the oak bark extract is present in a base of a spreadable carrier material, with the oak bark extract being present in the carrier at a concentration of from about 0.1% by weight to about 40% by weight, more preferably at a concentration of about 3-10% by weight since at concentrations below about 3% by weight, the ulcer takes longer to heal.

The carrier can be any suitable sterile, spreadable base material, which may include, for example, lanolin, petroleum jelly, polyalkylene glycols, such as polyethylene glycols, or mixtures thereof. The ointment may also contain stabilizers such as benzoic acid and salicylic acid.

In a particularly preferred embodiment, the ointment contains 3% by weight oak bark extract, 6% by weight benzoic acid, 3% by weight salicylic acid, with the balance being a mixture of polyethylene glycol-8 and polyethylene glycol-75.

In preferred embodiments, the ointment is applied on a daily basis to the ulcer so as to cover the ulcer after cleansing thereof.

The invention is illustrated by the following example, which is not intended to be limiting.

EXAMPLE

An ointment containing oak bark extract (3% by weight), benzoic acid (6% by weight), salicylic acid (3% by weight) in a base of polyethylene glycol-8 and polyethylene glycol-75 was evaluated in the treatment of Grade III and Grade IV decubitus ulcers, and compared to Debrisan ™, an ointment manufactured by Johnson and Johnson specifically for the treatment of Grade III decubitus ulcers.

The study was a randomized double blind, placebo controlled evaluation of oak bark ointment and its comparison to Debrisan in Grade III decubitus ulcers, and a double blind, placebo controlled evaluation of oak bark ointment in Grade III and Grade IV decubitus.

The number of patients completing the test were as follows:

|  | Grade III | Grade IV |
|---|---|---|
| Oak Bark Ointment | 16 patients | 4 patients |

| | Grade III | Grade IV |
|---|---|---|
| Placebo | 4 patients | 5 patients |
| Debrisan | 2 patients | |

The sequence of treatment was determined by a computer generated random number scheme. As patients were enrolled, the size of the ischemic ulcer was determined, which Patient Assignment Sheet shall be utilized to designate which cream formulation to be placed at the test site. The same test material was used for the duration of the patient's participation. Evaluation of the wound was done by the same Investigator following cleansing of the ulcer. The results are showing in Tables 1 and 2 below:

TABLE 1

| | Grade III Ulcers | | |
|---|---|---|---|
| PRODUCT | ULCER SITE | RESULT (Success-S Failure-F) | DAYS OF TREATMENT |
| Oak Bark Ointment | Heel | F | 42 |
| Oak Bark Ointment | Buttocks | S | 55 |
| Oak Bark Ointment | Coccyx | S | 77 |
| Oak Bark Ointment | Coccyx | S | 47 |
| Oak Bark Ointment | Coccyx | S | 115 |
| Oak Bark Ointment | Coccyx | S | 85 |
| Oak Bark Ointment | Coccyx | S | 49 |
| Oak Bark Ointment | Hand | S | 18 |
| Oak Bark Ointment | Hip | S | 77 |
| Oak Bark Ointment | Ankle | S | 63 |
| Oak Bark Ointment | Heel | S | 63 |
| Oak Bark Ointment | Coccyx | S | 70 |
| Oak Bark Ointment | Coccyx | S | 77 |
| Oak Bark Ointment | Shoulder | S | 115 |
| Oak Bark Ointment | Coccyx | F | 63 |
| Oak Bark Ointment | Coccyx | S | 70 |
| Debrisan | Coccyx | S | 63 |
| Debrisan | Shoulder | F | 21 |
| Placebo | Shin | F | 42 |
| Placebo | Coccyx | S | 63 |
| Placebo | Coccyx | F | 28 |
| Placebo | Coccyx/Buttocks | S | 56 |

TABLE 2

| | Grade IV Ulcers | | |
|---|---|---|---|
| PRODUCT | ULCER SITE | RESULT (Success-S Failure-F) | DAYS OF TREATMENT |
| Oak Bark Ointment | Shin | S | 91 |
| Oak Bark Ointment | Coccyx | S | 63 |
| Oak Bark Ointment | Coccyx | S | 49 |
| Oak Bark Ointment | Heel | S | 49 |
| Placebo | Hip | F | 28 |
| Placebo | Buttock | F | 70 |
| Placebo | Heel | S | 28 |
| Placebo | Hip | F | 28 |
| Placebo | Hip | F | 28 |

The analysis of the treatment results of Grade IV ulcers using oak bark ointment and the placebo were even more striking. The success percentage of oak bark ointment was 100% site healed or improving, whereas with the placebo the success rate was only 20%, one out of five patients healed or improving.

In examining the data on the results of the treatment of Grade III ulcers, complete healing occurred in 7 of the fourteen patients who responded favorably to the oak bark ointment. This healing process to completion took on the average, 57.5 days. Improvement from a Grade III to a Grade II, occurred with the 7 remaining patients treated with oak bark ointment on the average in 83.9 days. Evidently the general physical condition and the body's impaired healing properties was a major factor in the length of time of complete site healing. There was no apparent relationship between success or failure, length of healing time associated with the site of the ulcer.

This study indicates that oak bark ointment is extremely effective in the treatment of decubitus ulcers, regardless of the body site or the grade of ulcer (III or IV).

Oak bark ointment results, when compared to Debrisan or placebo, registers significant advantages, an 87% success rate compared to 50% for both Debrisan and the placebo. It is interesting that there is not a difference between the placebo, a lanolin base cream, and Debrisan which is designed specifically for the treatment of Grade II decubitus ulcers.

Oak bark ointment enjoyed a 100% success rate, when used in treating Grade IV ulcers, compared to the placebo's 20% success.

Half of the oak bark ointment patients with Grade III ulcers achieved complete healing in 57.5 days.

Of the Grade IV ulcers treated by oak bark ointment, one achieved complete healing in 63 days and the remaining three patients progressed from a Grade IV to a Grade II on the average in the same time span.

The treatment of Grade IV ulcers by use of the placebo, as stated previously, resulted in four failures out of five patients treated. Of those four failures, two developed infections at the body site. No oak bark patient developed an infection during the treatment period, either in the Grade IV or Grade II segments of the test.

Since many modifications, variations and changes in detail may be made the described embodiment, it is intended that all matter in the foregoing description be interpreted as illustrative and not in a limiting sense.

I claim:

1. A method of treating a skin ulcer, comprising applying to a skin ulcer of a patient in need of skin ulcer treatment, an ointment comprising a sterile base material containing a therapeutically effecting amount of an aqueous extract of oak bark ash from genus "Quercus".

2. The method of claim 1 wherein the oak bark ash is derived from bark of a species of Erythrobalanus.

3. The method of claim 1 wherein the oak bark ash is derived from bark of Red Oak, Black Oak, Scarlet Oak, Pin Oak or Willow Oak.

4. The method of claim 1 wherein the oak bark ash is derived from Red Oak bark.

5. The method of claim 1 wherein said ointment is applied to an ulcer selected from the group consisting of abrasion ulcers, decubitus ulcers and venostasis ulcers.

6. The method of claim 1 wherein said ointment is applied daily.

7. The method of claim 1 wherein said ulcer is cleansed prior to application of said ointment.

8. The method of claim 1 wherein said ointment is applied so as to cover said ulcer.

9. The method of claim 1 wherein an aqueous solution of said extract is present in said ointment at a concentration of from about 0.1% by weight to about 40% by weight.

10. The method of claim 9 wherein said concentration is about 3-10% by weight.

11. The method of claim 9 wherein said concentration is about 3% by weight.

12. The method of claim 1 wherein said ointment further contains a stabilizer selected from the group consisting of benzoic acid, salicylic acid and mixtures thereof.

13. The method of claim 12 wherein said ointment further contains a polyalkylene glycol.

14. The method of claim 13 wherein said polyalkylene glycol is selected from the group consisting of polyethylene glycol-8, polyethylene glycol-75 and mixtures thereof.

15. A method for treating a skin ulcer, comprising applying to a skin ulcer of a patent in need of skin ulcer treatment, an ointment comprising a sterile base material containing a therapeutic effective amount of an aqueous extract of oak bark ash from genus "Quercus", the extract being formed from oak bark of said genus "Quercus" by burning the oak bark to convert it to ash, mixing the ash with water to form a slurry, boiling the slurry, and filtering the slurry to form a filtrate containing said extract, said ointment being applied to said skin ulcer.

16. The method of claim 15 wherein said ash is cooled and an ash powder is obtained therefrom prior to mixing with said water, and about 1 part of said ash powder is mixed with about 4 parts of said water to form said slurry.

17. The method of claim 16 wherein said slurry is boiled for a period of from about 90 minutes to about 120 minutes.

18. The method of claim 17 wherein said filtrate is concentrated by heating the filtrate to a temperature of from about 150° F. to about 170° F. for from about 4 hours to about 10 hours to obtain an aqueous solution of oak bark extract.

19. The method of claim 18 wherein said filtrate is concentrated at a temperature of about 160° F.

20. The method of claim 15 wherein the oak bark ash is derived from bark of a species of Erythrobalanus.

21. The method of claim 15 wherein the oak bark ash is derived from bark of Red Oak, Black Oak, Scarlet Oak, Pin Oak or Willow Oak.

22. The method of claim 15 wherein the oak bark ash is derived from Red Oak bark.

23. The method of claim 15 wherein said ointment is applied to an ulcer selected from the group consisting of abrasion ulcers, decubitus ulcers and venostasis ulcers.

24. The method of claim 15 wherein said ointment is applied daily.

25. The method of claim 15 wherein said ulcer is cleansed prior to application of said ointment.

26. The method of claim 15 wherein said ointment is applied so as to cover said ulcer.

27. The method of claim 15 wherein an aqueous solution of said extract is present in said ointment at a concentration of from about 0.1% by weight to about 40% by weight.

28. The method of claim 27 wherein said concentration is about 3-10% by weight.

29. The method of claim 27 wherein said concentration is about 3% by weight.

30. The method of claim 15 wherein said ointment further contains a stabilizer selected from the group consisting of benzoic acid, salicylic acid and mixtures thereof.

31. The method of claim 30 wherein said ointment further contains a polyalkylene glycol.

32. The method of claim 31 wherein said polyalkylene glycol is selected from the group consisting of polyethylene glycol-8, polyethylene glycol-75 and mixtures thereof.

* * * * *

UNITED STATES PATENT AND TRADEMARK OFFICE
CERTIFICATE OF CORRECTION

PATENT NO. : 5,080,900
DATED : January 14, 1992
INVENTOR(S) : R. Thomas Stanley

It is certified that error appears in the above-identified patent and that said Letters Patent is hereby corrected as shown below:

Column 1, line 60, delete "It is", and insert --It has--.

Column 5, line 13, delete "patent", and insert --patient--.

Signed and Sealed this

Twenty-second Day of June, 1993

Attest:

MICHAEL K. KIRK

Attesting Officer

Acting Commissioner of Patents and Trademarks